United States Patent [19]
Yost

[11] Patent Number: 4,967,608
[45] Date of Patent: Nov. 6, 1990

[54] TEST CHAMBER FOR PARTICLE EMITTERS

[75] Inventor: Michael G. Yost, Suisun, Calif.

[73] Assignee: Ion Systems, Inc., Berkeley, Calif.

[21] Appl. No.: 346,073

[22] Filed: May 2, 1989

[51] Int. Cl.$^5$ ..................... G01N 33/00; G01N 15/10
[52] U.S. Cl. .................................. 73/866; 73/865.5; 377/10
[58] Field of Search ............... 73/865.5, 866; 364/555; 377/10, 11, 12

[56] References Cited

U.S. PATENT DOCUMENTS

| | | | |
|---|---|---|---|
| 4,154,088 | 5/1979 | Werner | 73/863.01 X |
| 4,154,111 | 5/1979 | Anderson et al. | 73/865.5 |
| 4,477,187 | 10/1989 | Pettit et al. | 356/349 X |
| 4,625,552 | 12/1986 | Johnson | 73/865.5 |
| 4,761,074 | 8/1988 | Kolsaka et al. | 356/338 X |

FOREIGN PATENT DOCUMENTS

| | | | |
|---|---|---|---|
| 157684 | 8/1985 | Japan | 377/10 |
| 137043 | 6/1986 | Japan | 73/866 |

OTHER PUBLICATIONS

Liu, BHY and Kinstley "Aerosol Charging . . . in Clean Rooms" J. of Environmental Sciences Mar./Apr. 87 pp. 42–46.
Blitshteyn and Shelton "Contamination . . . Emitters'-'Microcontamination, Aug. 1985 pp. 29–32.
Cooper, Miller, Wu; Deposition of Submicron Particles IBM Research Report RC 13722 5/26/88 pp. 1–26.
Donovan, Yamamoto et al. "Experimental Study . . . Gradients" 9th ICCCS Proceedings 1988, pp. 37–42.
Donovan et al. "Measuring Particle Emission . . . " Microcontamination Oct. 1987 pp. 36–39, 60–63.
Donovan et al. "Dependence of Particle . . . Potential" IES Proceedings 1987 pp. 473–478.
Donovan et al. "Polarity Dependence . . . Discharge" Microcontamination May 1986 pp. 38–49.
Fissan and Turner "Control of Particle Flux . . . Contamination" 9th ICCCS Proceedings 1988 p. 33–36.
Hinds "Aerosol Technology" John Wiley & Sons 1982, pp. 239, 302–305.
Rogers and Bailey "A Closed Chamber . . . Equipment" Microcontamination Feb. 1987, pp. 43–47, 66–67.
Inoue et al "Aersol Deposition on Wafer" 1988 Proceedings Inst of Environmental Sciences pp. 423–428.
Whitby et al "Dynamic Method . . . Purifiers" ASHRAE Trans. 89(2a) pp. 172–184 (No. 2771).
Suzuki and Izumoto "Effectiveness of . . . Clean Rooms" 1988 Proceedings Inst. of Environmental Sciences pp. 405–412.

Primary Examiner—Tom Noland
Attorney, Agent, or Firm—Phillips, Moore, Lempio & Finley

[57] ABSTRACT

A test chamber is disclosed that permits standardized measurement of particles in the chamber environment. A device or structure that is suspected of the emitting particles and which is desired to be tested is located within the chamber. The chamber environment is then controlled by the introduction of filtered air thereby permitting both static measurements of particle emissions from the device or structure and flow through measurements of particle emissions from the device or structure.

15 Claims, 7 Drawing Sheets

*FIGURE 6*
STATIC BOX PARTICLE TEST

FIGURE 7

TEST CHAMBER FOR PARTICLE EMITTERS

TECHNICAL FIELD

This invention discloses a chamber and a method for measuring particle emissions from articles. It particularly discloses a device that measures particle emissions from equipment associated with the manufacture of electronic devices.

BACKGROUND OF THE INVENTION

Semiconductor manufacturers must go to great lengths to maintain a clean processing environment and to prevent particle contamination of critical wafer surfaces. Sources of such particle contamination are myriad. In a relatively still air environment particles may emanate from moving machinery such as electric motors or robotic devices. In an environment where the air is rapidly moving, surface particles may literally be emitted by most anything. Once the particle is airborne, it becomes a potential contaminant whether it comes from a moving machine or from a surface. In either case it is prudent to eliminate or lessen the source of particles. Where the source cannot be eliminated, it is appropriate to reduce the deposition of airborne particles on surfaces. One way to do so is with bi-polar air-ionization.

A number of studies have identified electrostatic forces as having a major influence on the rate of particle deposition onto charged surfaces. In many instances electrostatic forces can be more significant than gravitational, aerodynamic, or thermal forces. Bipolar air ionization can effectively reduce surface charges, and as a result decrease the rate of particle deposition on critical product surfaces. Several tests have shown a significant improvement in surface particle counts on test wafers when the surface potential was reduced from 5 kV to <100 volts.

However, other reports indicate that some high voltage DC corona discharge ionizers themselves generate large numbers of submicron particles in the 0.003 to 0.03 micron range. The small size of these particles would allow the apparent contradiction with reports of lower surface contamination in ionized areas, since these small particles would remain undetectable by most surface scanning equipment.

The papers reporting particle generation have drawn criticism in several respects. Some results were based on accelerated testing at corona currents up to 50 times normal operating levels. Other tests failed to report such factors as the placement and grounding of the particle sampling probe, the air flow past the ionizer and probe, and the background particle counts. Some of the tests used emitter materials that ionizer manufacturers do not use because these materials erode rapidly. Particle emission from moving machinery such as robotics or electric motors, while known or suspected, is apparently not well reported.

Overall, the lack of standardization in the test methods prevented any comparison of the particle readings from different materials and articles including ionization devices. Finally, disagreement exists as to the source of the particles. For example, an analysis of the deposits formed on ion emitters in cleanrooms shows that the residue is nonmetallic and probably collected from some other source in the environment.

Ultrafine particle generation concerns manufacturers of equipment used in a cleanroom and their customers. Clearly a standardized test chamber and method is needed for measuring particle emissions from any equipment that is to be used in the manufacture of electronic equipment.

In the past a number of methods have been used to obtain measurement of particle emission from semiconductor processing equipment. These methods include:

(1) Local sampling within the cleanroom.

The most common method has been in situ sampling that is done within a cleanroom. A sampling probe attached to an aerosol particle counter is used to draw an air sample near the device being measured. The total particles being emitted are calculated based on the sample counts. This method fails to define the probe location and dilution volume which the source operates into. As a result, it produces highly variable results.

(2) Sampling with a flow-through chamber.

In this method the device is placed within a tunnel with a known flow rate of HEPA (High Efficiency Particulate Air) filtered air continuously moving past it. A sampling tube is placed downstream from the source to measure the concentration of particles. Device performance can be evaluated based on a clean air standard such as Federal Standard 209D. With adequate air mixing this method can provide reproducible results, but it lacks the sensitivity to detect low source emission rates.

(3) Sampling within a static chamber.

In this method the device is enclosed in a chamber where the particle concentration is measured over time. The particle concentration is allowed to reach steady state levels to determine the particle generation rate of the device. This technique provides reproducible results and has the highest sensitivity for detecting low levels of particle emissions.

It is an object of this invention to provide a test chamber that has no internal mechanical devices.

It is a further object of this invention to provide a test chamber that has an extremely low particle background count.

It is still another object of this invention to provide a chamber that has a predictable particle decay constant.

The invention is a device for measuring particles emitted from an article; it includes a closed chamber defining a cavity sufficiently large to accept the article. The chamber has a first and a second end and filters located such that air may be introduced into the chamber at one end and removed at the second end. A source of compressed air is also provided with filters so that filtered compressed air can also be communicated to the cavity. Finally, a particle counter is included that can detect particles as small as 0.003 microns.

This invention is a unique chamber design that can provide measurements for either the flow-through or static chamber test methods. Details of the hardware, software, and mechanical aspects of the test apparatus, are presented with test results that demonstrate the performance of the chamber.

DETAILED DESCRIPTION OF A PREFERRED EMBODIMENT

Figure 1:
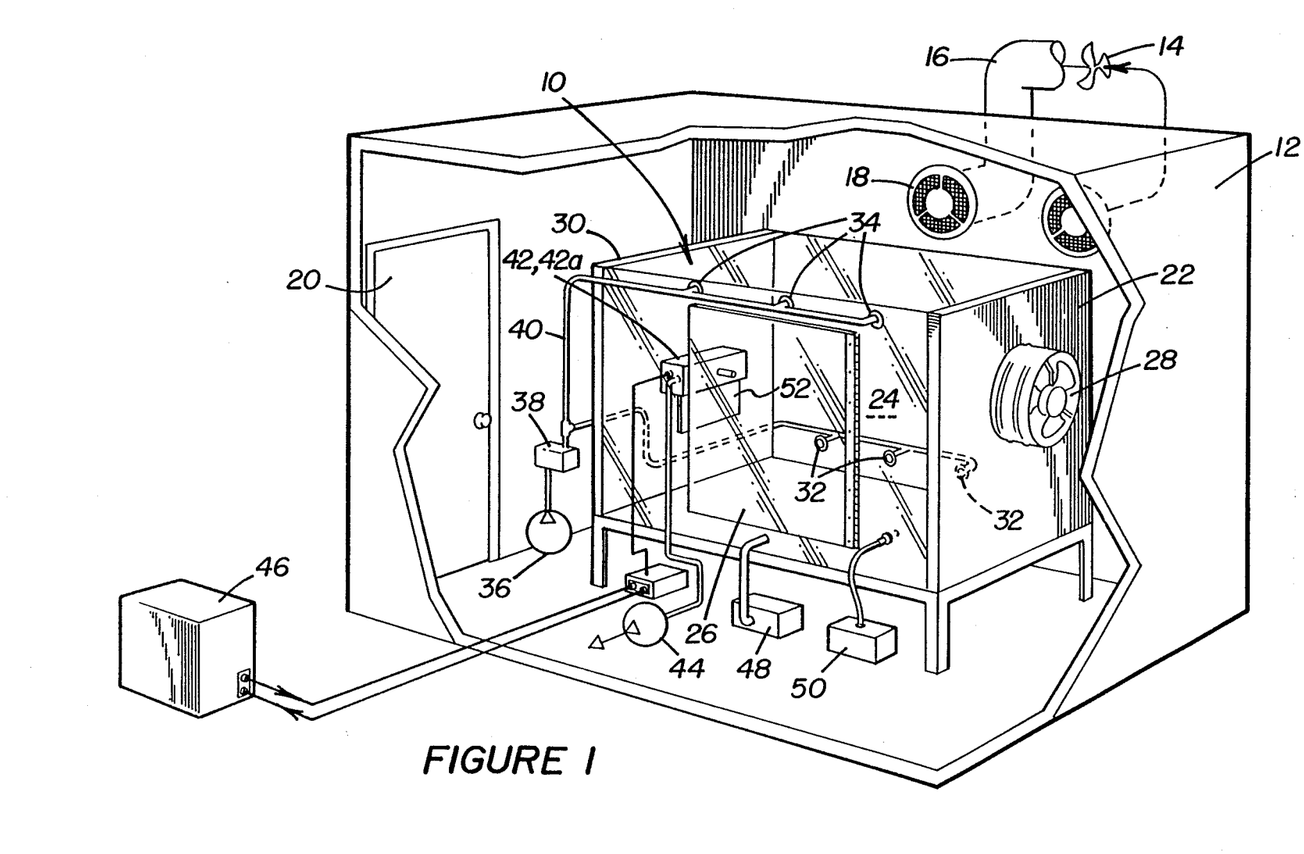
FIG. 1 is a perspective view of the chamber disclosed herein shown within a room which is broken away for illustration purposes.

Referring to FIG. 1, a measurement chamber 10 is located within a room 12 which for purposes of illustration is shown broken away. Room 12 is an environmentally controlled room wherein air is supplied by means of a fan 14 through a duct 16 which includes an air filtering system 18. Air filtering system 18 includes a VLSI (Very Large Scale Integration) grade HEPA (High Efficiency Particulate Arrestor) filters such as available from Flanders Filters, Inc. located in Washington, S.C. Air filtering system 18 generally recirculates ambient air in room 12.

Access to room 12 is available through a normally closed door 20 to prevent unnecessary entry of contaminates or particles. If door 20 is closed and ambient air is provided to room 12 through air filtering system 18, the air contained in the room normally carries a relatively low particle count.

Measurement chamber 10 is located within room 12 and thus is provided with a relatively clean environment at the outset. Measurement chamber 10 defines an internal cavity 24 of a predetermined volume. Cavity 24 is formed sufficiently large to accept an article or piece of equipment that is known or suspected of being a particle emitter. Such articles may be found in existing clean rooms or it may be appropriate to use such an article in an existing clean room. However, before the article is placed in the clean room it is appropriate to determine if there is any particulate emission from that article. For example, small electric motors may very well give off aerosol size particles of metal or oil during normal operation. Such particulate matter could be ruinous to the manufacturer of wafers or electronic chips.

Measurement chamber 10 is constructed of a material that may be readily cleaned on the inside surfaces. A door 26 is affixed to one side of chamber 10 to provide access to the interior thereof. The door, when closed, is sealed to the rest of the chamber utilizing a rubber gasket to prevent ambient air in room 12 from entering the chamber during the test.

At least two matching VLSI grade HEPA filters, again available from Flanders Filters in Washington, S.C. are utilized to provide flow through air. The first filter 22 of the VLSI grade HEPA filter is affixed at one end of chamber 10 and includes an exterior fan unit 28 to provide a source of filtered air to the interior of chamber 10. At the opposite end of chamber 10 is a similar VLSI grade HEPA filter 30 to permit the air to be exhausted from chamber 10. It is noted that the filters at either end of chamber 10 are the type that have an inlet and outlet side for efficient filtering. It is to be understood that the inlet side of filter 22 is on the room side of chamber 10 while the inlet side of filter 30 is on the cavity 24 side of filter 30. In large test chambers, it may be appropriate to provide additional HEPA filters.

A key feature of chamber 10 is the inclusion of plurality of air jets 32 and 34. Air jets 32 and 34 are located on opposite sides of cavity 24 preferably with one set located in the lower portion of cavity 24 and the other set in the upper portion of cavity 24. Further, the number of air jets 32 and 34 may vary depending upon the size of chamber 10. It is sufficient to have only one of the type 32 and one of the type 34. That is to have at least one air jet on opposite walls along the top and the bottom face of the chamber. In small chambers, a single jet may be sufficient. The purpose of these jets as opposed to the flow through air provided by fan unit 28 is to provide about two air changes of air per hour as make up air and to ensure a thorough mixing of the atmosphere contained in the box in the chamber 10. The supply of air is provided from a compressor 36 which provides air to a filter unit 38.

Figure 7:
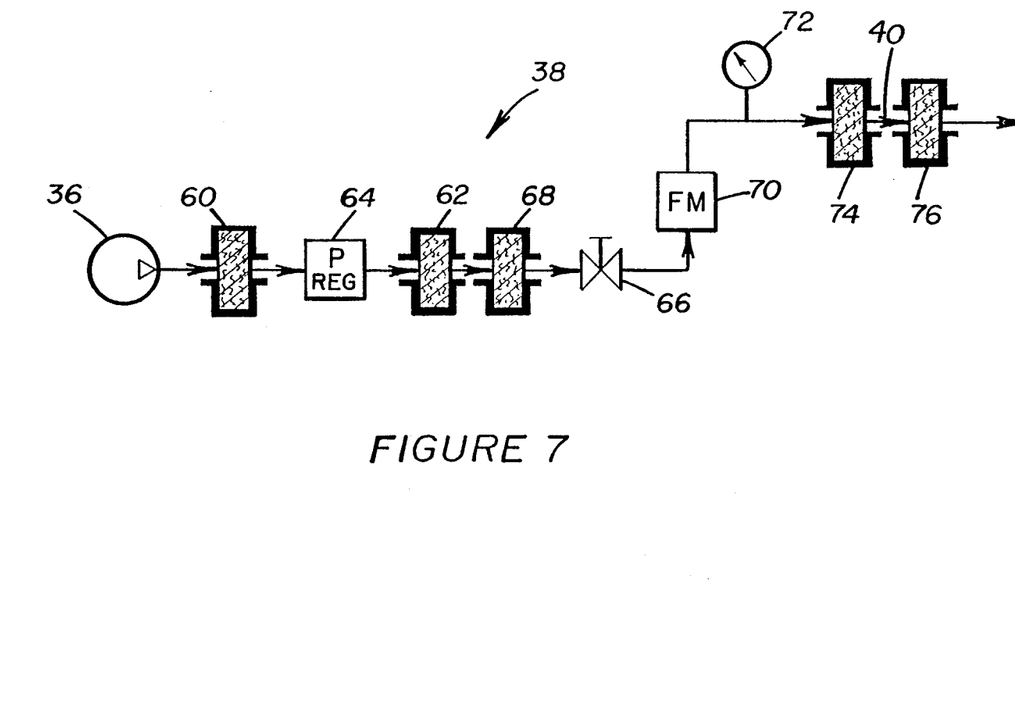
FIG. 7 is a schematic of the compressed air system used for make up air.

Filter unit 38 is shown in detail in FIG. 7. Air is provided to at least a five stage filtering system. The first filter 60 is preferably a 5 micron filter, as is the second filter 62. Interposed between filters 60 and 62 is a pressure regulator 64. A needle valve 66 controls the flow of air leaving a third filter 68 which is just downstream of filter 62. Filter 68 is preferably a 0.1 micron filter. A flowmeter 70 is downstream of needle valve 66, with a pressure gauge 72 next in line. Finally a glass filter 74 communicates the air to conduit 40 which communicates the air to jets 32 and 34. Located at each jet are the final filtration stages which consists of at least one 0.02 micron membrane filters 76 exhausting directly into the box. These filters are available from Millipore Corp., 80 Ashby Road, Bedford. Mass. 01730 This provision, in the static test, provides a slight positive pressure within cavity 24 thus preventing outside particles from leaking into measurement chamber 10.

What has been described to this point is the minimum structure to provide either a static chamber or a flow through chamber for the testing of equipment. What remains to be described is the equipment necessary to conduct the test.

Particle counting is accomplished with a counter 42. Counter 42 includes at least a capability of detecting particles at least as small as 0.005 microns. Such counters are available from TSI, Inc. at 500 Cardigan Road, St. Paul, Minn. In particular, Model 3760 condensation nucleus counter detects particles larger than 0.014 microns at a sample rate of 1.42 liters per minute. This particle counter, as can be seen from FIG. 1, sits inside cavity 24 and draws air into the counter directly from the cavity 24. A vacuum pump 44 provides the necessary air flow through the particle counter. The location of the particle counter 42 would be important to the test, particularly, the location of the particle counter in relation to the article to be tested. In the particular example utilized, the particle counter is one meter from the piece of equipment being tested.

Output from the particle counter 42 is communicated to a computerized system 46 for appropriate manipulation. It has been found that the particle counts may be logged into a computerized system that selects the particle count at a predetermined interval such as every two minutes and saves the data in a memory storage. The data is then available for manipulation in commercial spread sheet programs.

In addition to the aforedescribed particle counter, an additional counter may also be necessary to count larger size particles. Such a counter which shall be identified as 42A is available from Particle Measuring Systems located at 1855 South 57th Court, Boulder, Colo. 80301. This particular device measures particles larger than 0.1 microns and further classifies them into size categories.

During the flow through tests, it is appropriate to measure the velocity of air passing through cavity 24. Such is done with thermoanemometer 50. Such an instrument is available from Kurts Instruments, Inc. at 2411 Garden Road, Monterey, Calif. 93940.

In the event an air ionizer is being tested in the chamber, it is appropriate to include a field meter to read charges in the vicinity of the particle counter. Such a meter is shown as meter 52 and is available from Trek, Inc., 3932 Salt Works Road, Medina, N.Y.

In order to monitor the test environment when testing an ionizer, it is also appropriate to include an ozone meter that measures ozone concentrations to the particle per billion level. Such a meter is shown as ozone meter 48 and is available from Dasibi Environmental Corporation in Glendale, Calif.

Figure 2:
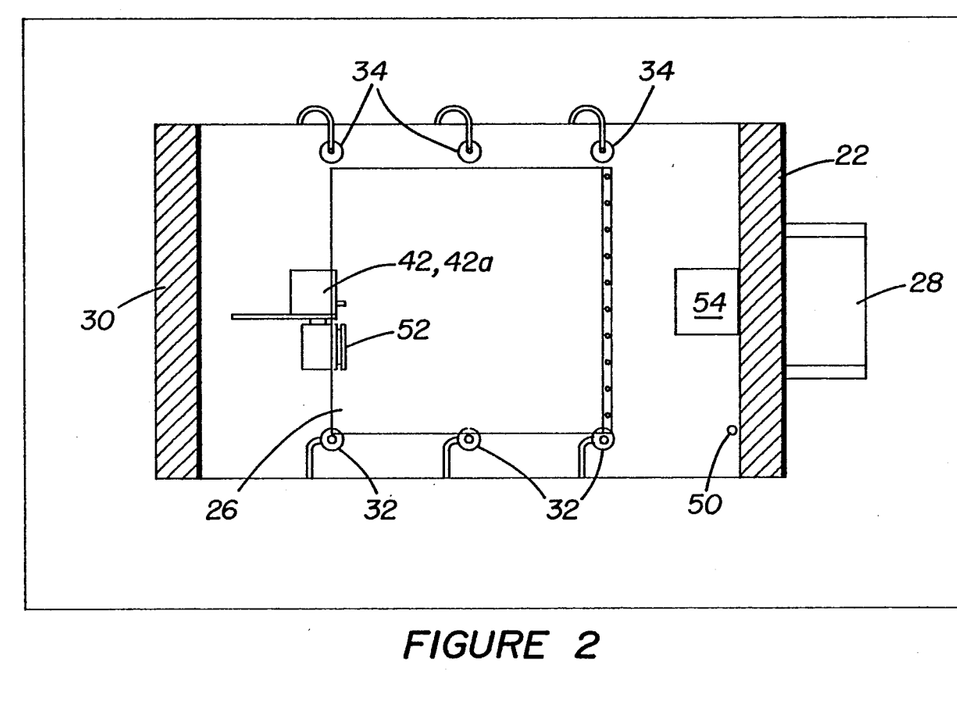
FIG. 2 is a schematic cross sectional view of the chamber shown in FIG. 1.

In referring now to FIG. 2, a view of chamber 10 is shown in elevation. In FIG. 2, the article 54 to be tested is illustrated.

CHAMBER DYNAMICS

When used as a static test chamber, the chamber 10 can be modeled as a well mixed box. This technique permits the test results to be used to determine the particle generation rate of the article 54. The basic differential rate equation for the concentration of a contaminant in a well-mixed box is given by:

$$V \frac{dC}{dt} = P - kC - QC \quad (1)$$

where
 V = chamber volume ($L^3$)
 P = particle production $t^{-1}$
 C = particle concentration $L^{-3}$
 k = wall loss rate ($L^3 t^{-1}$)
 Q = Make-up air flow rate ($L^3 t^{-1}$)

Applying appropriate initial conditions, equation 1 can be integrated to obtain some familiar equations describing the filling and emptying of the box. Assuming a constant particle production begins at t=0, when C=0 the concentration rise toward steady state is given by:

$$C(t) = \frac{P}{Q^*}\left[1 - \exp\left(\frac{-tQ^*}{V}\right)\right] \quad (2)$$

where
 $Q^* = k + Q$ = the equivalent air flow rate As t becomes long, the exponential term becomes small and equation 2 simplifies to the steady state equation:

$$P = C_{2S} Q^* \quad (3)$$

If the chamber is filled with particles and article 54 is suddenly switched off, (assuming article 54 is powered) the concentration will decay toward zero according to:

$$C(t) = C_o \exp\left(\frac{-tQ^*}{V}\right) \quad (4)$$

Equations 2-4 show that the chamber has a transient behavior similar to a first order RC filter. When an article with variable particle emission is placed in the box, the concentration fluctuations will be damped with a time constant $$\tau = \frac{V}{Q^*} \quad (5)$$

Equation 2 implies that one needs to wait about 2 to 3 time constants to approach (within 5%) steady state conditions. Equation 4 indicates that slope of the decay curve is the inverse of the chamber time constant. Agglomeration losses have been ignored since the particle concentrations are never allowed to reach levels where Smoluchowski coagulation becomes significant. The above equations assume perfect mixing in the chamber and constant wall losses. How closely the real chamber approaches this ideal behavior depends on how well these conditions are met.

TEST METHODS

The chamber 10 design allows for testing in either a flow-through state or in a static state. In both cases particle levels are monitored continuously during the test sequence. The flow-through arrangement surrounds the article 54 with HEPA filtered air, thus simulating the actual operating conditions with article 54 mounted in a cleanroom. For this test, the HEPA fan unit 28 is switched on, and after a 30 minute purge period, the article 54 is switched on to begin the test.

The static box test sequence is slightly more complicated than the flow through test. This test also begins with a 30 minute purge period with only the HEPA fan unit 28 operating. The HEPA fan unit 28 is then shut off and the background count is checked for 60 minutes with only the make-up air provided through air jets 32 and 34 on. Then the HEPA fan unit 28 is switched off so the article operates with only the make-up on. This portion of the test typically lasts 1 to 3 days, and measures the particle production rate. Air changes in chamber 10 should at a rate of between 2 and 8 changes each hour using the air make up system. Air regulation is accomplished with the filter system 38 and in particular regulator 64, needle valve 66 and flowmeter 70. During the final 120 minutes of the test, the article is switched off and the particle concentration is allowed to decay. The decay period provides a direct measure of the particle residence time in the chamber after the article has equilibrated the charge in the chamber.

The test chamber 10 must have very low background counts that remain stable during the entire test period. After initial assembly, the chamber walls should be wiped clean periodically with methanol while running the HEPA fan unit 28 and the make-up air system 32 and 34. This process should initially be repeated for several days. Finally, the HEPA fan unit 28 should be turned off leaving only the make-up air operating.

Figure 3:
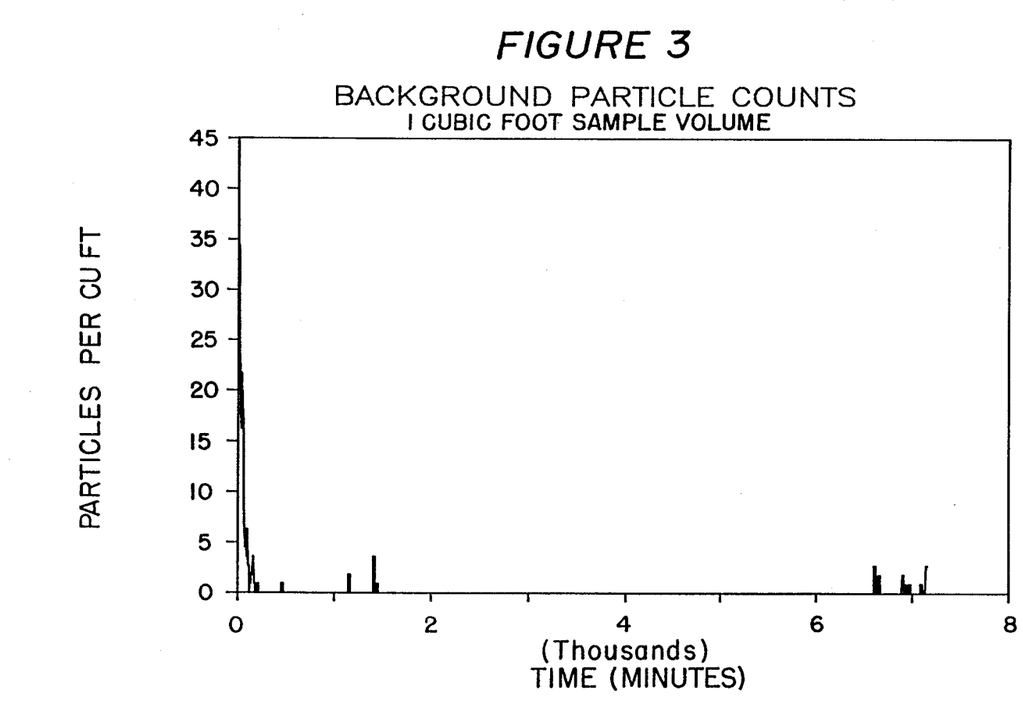
FIG. 3 is a plot of the background particle count in the chamber after purging.

After the initial treatment, the chamber 10 easily maintains low background counts. Typically, the background is less than one count per hour on counter 42 with long periods of zero counts. FIG. 3 shows a typical background count recorded over a 5 day period. The average concentration recorded by the counter 42 during a test was less than 0.03 particles/L (<1 PPCF). The chamber door 26 can be opened while keeping the HEPA fan unit 28 on, and after a brief 30 minute purge period, the long-term background will return to previous levels. (The initial spike at the beginning of the graph is the end of a previous run.)

Operating the chamber 10 (having a length of 1.8 m, a height of 0.6 lm and a width of 1.22 m) in the flow-through mode greatly increases the dilution air flow. The air velocity has been measured at 16 points in a vertical plane at 30 cm from the HEPA filter 28 and 130 cm from the filter. These locations correspond to the position of article 54 and the particle counter 42 inlet. The air velocity at the counter 42 averaged 28 cm/s (55 FPM)±19%. The average volume flow rate through the chamber 10, calculated from these readings, was 12,460 L/min (440 CFM). Thus the flow-through mode provides about 200 times more dilution air than the static box.

Figure 4:
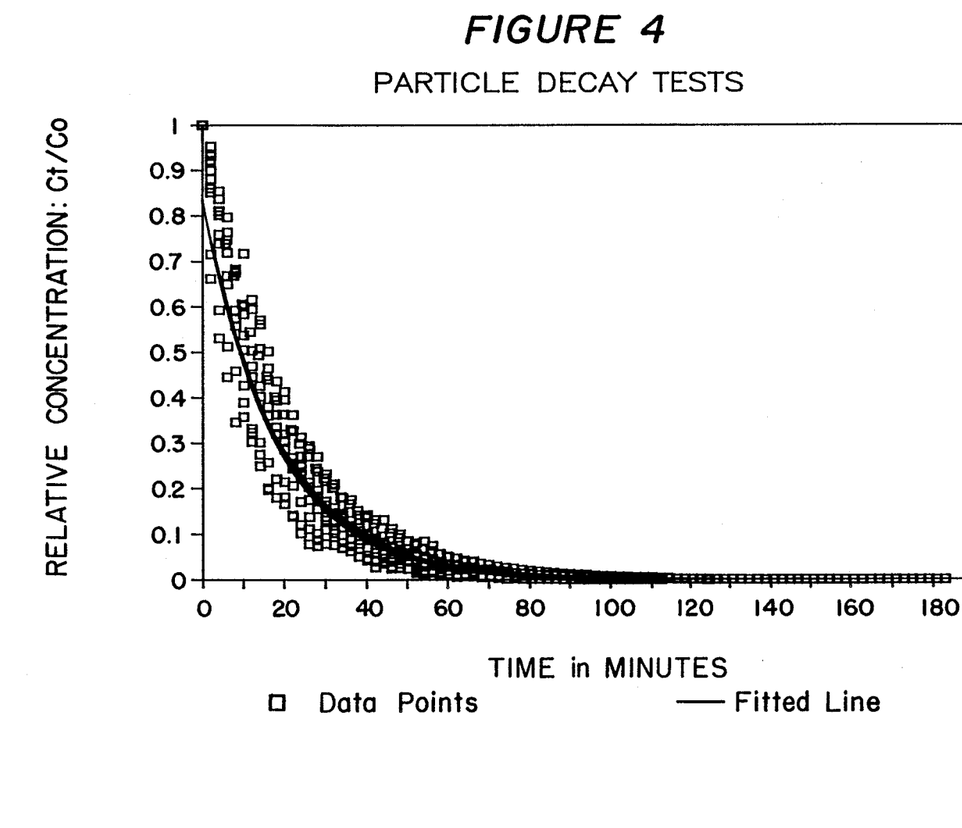
FIG. 4 is a plot showing decay in a static chamber.

Decay tests were conducted in the same chamber 10 to determine the wall losses and time constant of chamber 10 when used as a static chamber. Filtered room air was introduced into the box to create particle concentrations up to $10^5$ per L ($3 \times 10^5$ PPCF). Other tests were conducted at lower particle levels below about $10^3$ per L ($3 \times 10^4$ PPCF). The make-up air remained constant in all cases at 60 L/min. A total of ten decay curves were normalized for initial concentration and a least squares semi-log regression line was fitted to the data. The fitted line slope was 0.057 ($R^2 = 0.86$), giving a box time constant of 17.5 minutes and a Q* value of 77.5 L/min. FIG. 4 shows a plot of the particle decay data and the fitted line. Chambers of other dimensions would, of course, have different time constants.

Figure 5:
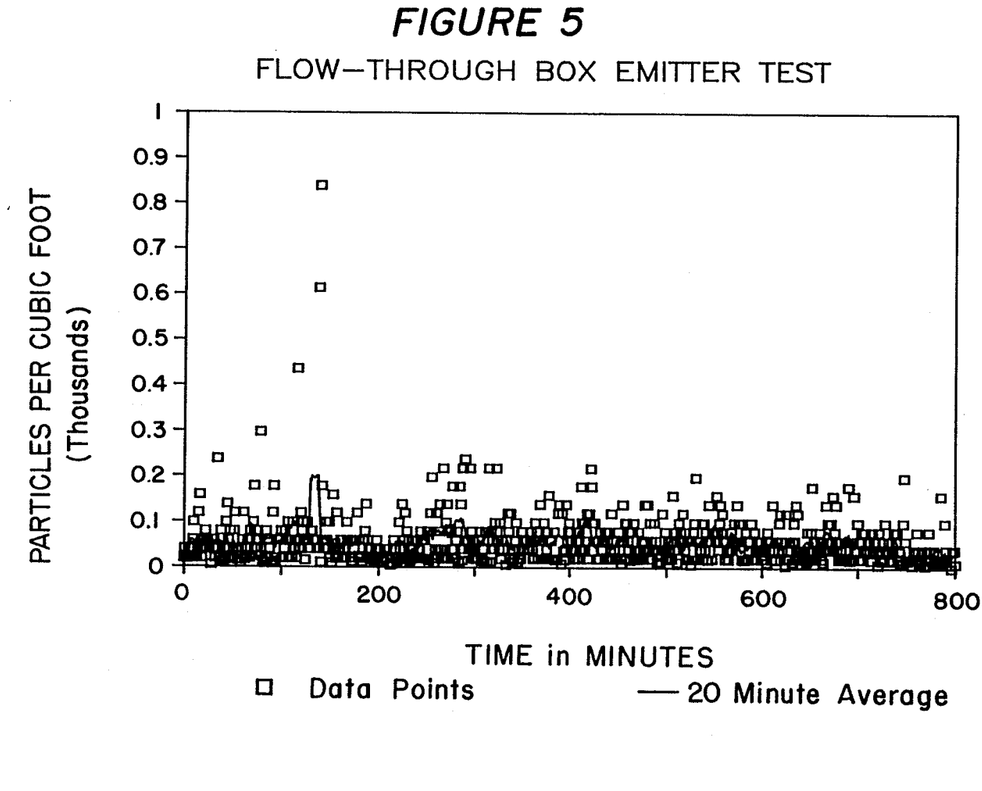
FIG. 5 is a plot of particles per cubic foot emitted from an air ionizer in the Flow Through mode.

Two plots are provided to illustrate the operation of the chamber 10 in each test mode. FIG. 5 shows the results of an article such as an air ionizer tested in the flow through mode. The particles were measured using the counter 42, sampling a volume of 2.8 L every 2 minutes (0.05 CFM). The plot shows a very "noisy" appearance, indicating that the particle production was quite erratic. The average concentration during the test was 2 particles/L (55 PPCF). A 20 minute moving time average line is also shown on the plot.

Figure 6:
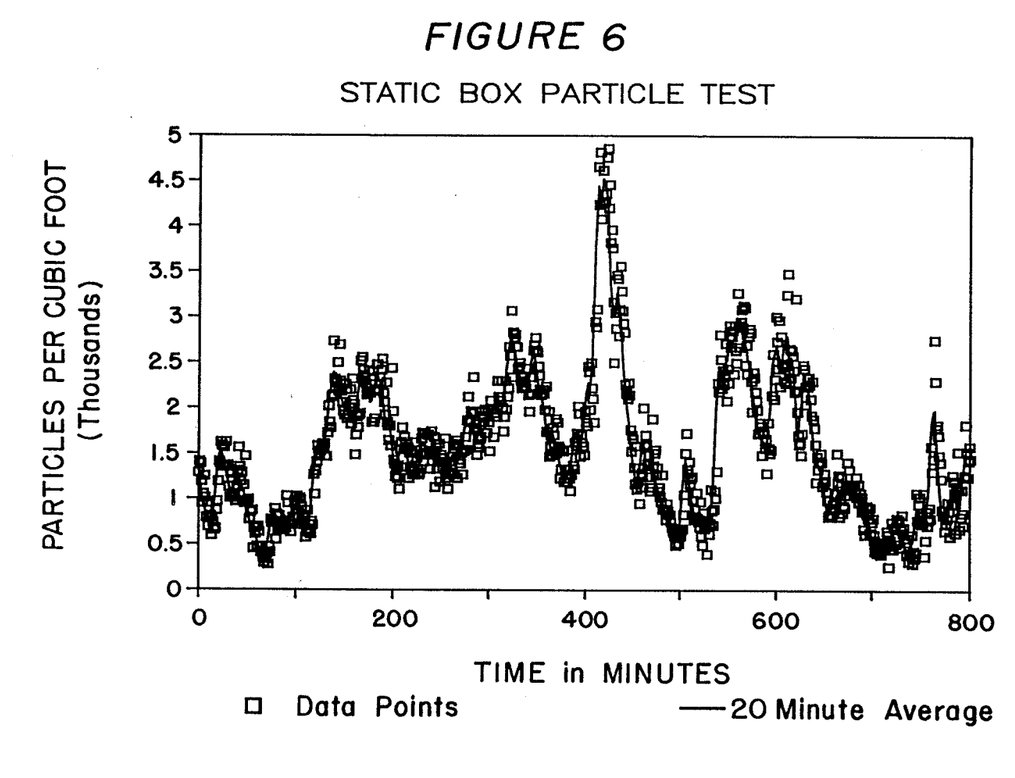
FIG. 6 is a plot of particles per cubic foot emitted from an air ionizer in the static mode.

FIG. 6 presents a plot of the results of the same air ionizer tested in the static chamber. The particle sampling conditions and other factors remain the same as in the previous plot. The much higher particle concentrations clearly show that the sealed box provides superior sensitivity. The average particle concentration during this test was 55 particles/L (1570 PPCF). The plot also illustrates the transient damping provided by the static box. The 20 minute average line closely follows the peaks and valleys in concentration, showing that the box does behave like a low pass filter with a time constant of 18 minutes.

The results demonstrate that the chamber 10 is a sensitive tool for measuring particle emissions. This design has advantages over previous methods, since it can operate as a static chamber or flow through chamber. Using filtered air jets 32 and 34 to stir the box, avoids the additional contamination or particle losses contributed by mixing fans. While the static box is a more sensitive particle detector, it should be remembered that the flow through chamber 10 is more representative of the actual operating conditions.

While this invention has been described in relation to a specific embodiment, it should not be so construed. Rather it is limited only with respect to the following claims.

I claim:

1. A device for measuring particles emitted from an article, the device comprising:
    a closed chamber defining a cavity sufficiently large to accept the article, the chamber having a first end and a second end and defining at least one port between said first and said second end;
    first filter means for introducing filtered air into said chamber through said first end;
    second filter means for permitting air to leave said chamber at said second end;
    a source of compressed air;
    means for filtering said compressed air;
    means for communicating said filtered compressed air to said at least one port of said chamber;
    means for detecting particles larger than 0.003 microns; and
    means for counting the detected particles for predetermined period of time.

2. The device of claim 1 further including means for measuring the air flow within the cavity from the first end to the second end.

3. The device of claim 1 further including means to regulate the flow of compressed air.

4. The device of claim 3 wherein the means for filtering the compressed air includes at least one filter upstream of the means to regulate the flow of compressed air and at least one filter downstream of the means to regulate the flow of compressed air.

5. The device of claim 4 wherein the means for filtering the compressed air further includes a port filter located at the at least one port.

6. The device of claim 1 wherein the closed cavity has a first side and a second side both interposed between and connecting said first and second ends; said at least one port located in said first side.

7. The device of claim 6 further defining a second port, located in said second side; said means for communicating filtered compressed air to at least one part of said chamber includes means for simultaneously communicating filter compressed air to all ports of said chamber.

8. The device of claim 7 wherein said cavity has a volume V and further wherein the means to regulate the flow of compressed air permits a flow of at least one volume V and no more than ten volumes V per hour to said chamber.

9. The device of claim 8 wherein the closed chamber includes an access door mounted in one side.

10. The device of claim 9 wherein the means for communicating filtered compressed air to said chamber includes a pressure regulator whereby pressure in said chamber can be maintained slightly above ambient pressure.

11. The device of claim 1 wherein the means for detecting particles comprises:
    a particle detector positioned in said chamber; a vacuum pump located outside said chamber
    conduit means for communicating a vacuum from said vacuum pump to said particle detector whereby chamber air may drawn into said particle detector to enable particles to be detected with said chamber air then being exhausted from said particle detector by said vacuum pump.

12. The device of claim 11 wherein said means for counting the detected particles for a predetermined period of time includes a microprocessor located outside said chamber and in communication with said particle detector.

13. A system for measuring particles emitted from an article comprising:
  a closed room having openable access and a recirculating filtered air system; and, a device located within said closed room, said device consisting of:
  a closed chamber defining a cavity sufficiently large to accept the article, the chamber having a first end and a second end and defining the least one port between said first and said second end;
  first filter means for introducing filtered air into said chamber through said first end;
  second filter means for permitting air to leave said chamber at said second end;
  a source of compressed air;
  means for filtering said compressed air;
  means for communicating said filtered compressed air to said at least one port of said chamber;
  means for detecting particles larger than 0.003 microns and
  means for counting the detected particles for predetermined period of time.

14. The device of claim 13 further including means for measuring the air flow within the cavity from the first end to the second end.

15. The device of claim 13 further including means to regulate the flow of compressed air.

* * * * *

UNITED STATES PATENT AND TRADEMARK OFFICE
CERTIFICATE OF CORRECTION

PATENT NO. : 4,967,608
DATED : November 6, 1990
INVENTOR(S) : Michael G. Yost

It is certified that error appears in the above-identified patent and that said Letters Patent is hereby corrected as shown below:

Column 5, line 63, delete "$P=C_{28}Q*$" and insert -- $P = C_\infty Q*$ --.

Signed and Sealed this

Third Day of March, 1992

*Attest:*

HARRY F. MANBECK, JR.

*Attesting Officer*      *Commissioner of Patents and Trademarks*